United States Patent
Kamilov et al.

(10) Patent No.: US 10,571,408 B2
(45) Date of Patent: Feb. 25, 2020

(54) SYSTEM AND METHOD FOR DETERMINING STRUCTURE OF MATERIAL

(71) Applicant: Mitsubishi Electric Research Laboratories, Inc., Cambridge, MA (US)

(72) Inventors: Ulugbek Kamilov, Cambridge, MA (US); Dehong Liu, Lexington, MA (US); Hassan Mansour, Boston, MA (US); Petros T. Boufounos, Arlington, MA (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 199 days.

(21) Appl. No.: 15/066,260

(22) Filed: Mar. 10, 2016

(65) Prior Publication Data
US 2017/0261538 A1    Sep. 14, 2017

(51) Int. Cl.
*G06N 3/02* (2006.01)
*G01N 22/00* (2006.01)
*G06N 3/08* (2006.01)

(52) U.S. Cl.
CPC ............ *G01N 22/00* (2013.01); *G06N 3/084* (2013.01)

(58) Field of Classification Search
CPC ..... G01R 27/2623; G01R 33/443; G06N 3/02
See application file for complete search history.

(56) References Cited

U.S. PATENT DOCUMENTS

| | | | |
|---|---|---|---|
| 5,729,660 A | 3/1998 | Chiabrera et al. | |
| 7,809,427 B2 | 10/2010 | Winters et al. | |
| 2008/0129298 A1* | 6/2008 | Vaughan | G01R 33/5612 324/322 |

(Continued)

FOREIGN PATENT DOCUMENTS

CN    102955159 A    7/2014

OTHER PUBLICATIONS

Svozil et al. "Introduction to multi-layer feed-forward neural networks", Chemometrics and Intelligent Laboratory Systems 39 (1997) 43-62.*

(Continued)

*Primary Examiner* — Thomas L Dickey
(74) *Attorney, Agent, or Firm* — Gennadiy Vinokur; James McAleenan; Hironori Tsukamoto

(57) ABSTRACT

A method propagates a pulse of wave through the material to receive a set of echoes resulted from scattering the pulse by different portions of the material and simulates a propagation of the pulse in the material using a neural network to determine a simulated set of echoes. Each node in a layer of the neural network corresponds to a portion of the material and assigned a value the permittivity of the portion of the material, such that the values of the nodes at locations of the portions form the image of the distribution of the permittivity of the material. The connection between two layers in the neural network models a scattering event. The method updates the values of the nodes by reducing an error between the received set of echoes and the simulated set of echoes to produce an image of the distribution of the permittivity of the material.

22 Claims, 9 Drawing Sheets

(56) References Cited

U.S. PATENT DOCUMENTS

2012/0139541 A1* 6/2012 Weiss .................. G01R 33/583
324/318

OTHER PUBLICATIONS

Kamal Belkebir and Anne Sentenac. High-resolution optical diffraction microscopy. J. Opt. Soc. Am. A, 20(7)1223-1229, Jul. 2003.
W. C. Chew and Y. M. Wang. Reconstruction of two-dimensional permittivity distribution using the distorted Born iterative method. IEEE Trans. Med. Imag., 9(2):218-225, Jun. 1990.
R. E. Kleinman and P. M. van den Berg. A modified gradient method for two-dimensional problems in tomography. J. Comput. Appl. Math., 42(1):17-35, 1992.
R. E. Kleinman and P. M. van den Berg. An extended range-modified gradient technique for profile inversion. Radio Sci., 28(5):877-884, Sep.-Oct. 1993.
A. G. Tijhuis. Born-type reconstruction of material parameters of an inhomogeneous, lossy dielectric slab from reflected-field data. Wave Motion, 11(2):151-173, May 1989.
P. M. van den Berg and R. E. Kleinman. A contrast source inversion method. Inv. Probl., 13(6):1607-1620, Dec. 1997.
Y. M. Wang and W. C. Chew. An iterative solution of the two-dimensional electromagnetic inverse scattering problem. Int. J. Imag. Syst Tech., 1:100-108, 1989.

* cited by examiner

SYSTEM AND METHOD FOR DETERMINING STRUCTURE OF MATERIAL

FIELD OF THE INVENTION

This invention relates to sensing systems and methods, and more specifically to system and method for determining an image of a distribution of permittivity of a material.

BACKGROUND OF THE INVENTION

Knowledge of the spatial distribution of the dielectric permittivity within a material is important for many applications such as microwave imaging, biomicroscopy, medical imaging, through-the-wall imaging (TWI), infrastructure monitoring, and seismic imaging. In particular, determination of permittivity enables the visualization of the internal structure of the material and characterization of its physical properties. For example, in microwave imaging permittivity provides the structure and properties of objects in the material. In biomicroscopy, the permittivity allows to visualize the internal cell structure in three-dimensions. In TWI, the permittivity allows to learn the dielectric properties of the wall and to use that information to compensate for the delay of the signal propagating through the wall.

In a typical scenario, a transmitter emits a signal such as an electromagnetic (EM) or light pulse, which propagates through the material, reflects off various structures inside the material, and propagates to a receiver antenna array. The composition of the material is then visualized by numerically generating an image that represents the distribution of the permittivity in the material. However, depending on the type of material, the received signal often resulted from the multiple reflections of the propagating pulse due to multiple scattering from the structures in the material, which results in artifacts that clutter the reconstructed image.

Accordingly, there is a need for a method determining an image of a distribution of permittivity of a material that accounts for the multiple scattering of the pulse of light propagating through the material. However, the multiple scattering of the pulse affects the pulse in a non-linear manner, making such a determination more difficult.

SUMMARY OF THE INVENTION

Some embodiments of the invention are based on realization that scattering of a pulse of wave propagated through a material of an object can be represented by a neural network with varying functions of the nodes of the network and fixed numeric weights connecting the nodes. The functions of the nodes represent permittivity of different portions of the material and the weights of the connections represent the physics of scattering the pulse by corresponding portions of the material. Such a neural network can capture the nonlinearity of scattering the pulse by different portions of the material in a manner allowing determining the permittivity of the material of the object from effects of the permittivity on the result of the scattering.

The neural networks are a family of models inspired by biological neural networks and are used to estimate or approximate functions that can depend on a large number of inputs and are generally unknown. The neural networks are generally presented as systems of interconnected nodes or "neurons" that exchange messages between each other. Each node is associated with a function for transforming the message. This function is usually non-linear to form a non-linear part of message transformation. Each connection between the nodes is associated with a numeric weight for scaling of the messages to form a linear part of message transformation. Typically, the functions are fixed and predetermined for all nodes, e.g., selected by a designer of the neural network. Examples of the functions typically selected for the nodes include the sigmoid and rectifier functions. In contrast, the numeric weights are different and tuned based on experience, making the neural network adaptive to inputs and capable of learning.

However, in the neural network used by different embodiments of the invention, such a relationship is reversed, i.e., the functions of the nodes are varied and determined during the training of the neural network, and the numeric weights of the connections between the nodes are fixed. Some embodiments of the invention are based on recognition that regardless of such a reverse relationships, the values of the nodes of the neural network can be learned using a back-propagation within amount of time comparable with the amount of time required for training the usual neural networks.

Accordingly, one embodiment of the invention discloses a method for determining an image of a distribution of permittivity of a material. The method includes propagating a pulse of wave through the material to receive a set of echoes resulted from scattering the pulse by different portions of the material; simulating a propagation of the pulse in the material using a neural network to determine a simulated set of echoes, wherein each node in a layer of the neural network corresponds to a portion of the material and assigned a value the permittivity of the portion of the material, such that the values of the nodes at locations of the portions form the image of the distribution of the permittivity of the material, and wherein connections between layers in the neural network models scattering events; and updating the values of the nodes by reducing an error between the received set of echoes and the simulated set of echoes to produce the image of the distribution of the permittivity of the material. At least some steps of the method are performed by a processor.

Another embodiment of the invention discloses a permittivity sensor for determining an image of a distribution of permittivity of a material, including at least one transceiver to propagate a pulse of wave through the material and to receive a set of echoes resulted from scattering the pulse by different portions of the material; and a processor to simulate a propagation of the pulse in the material using a neural network to determine a simulated set of echoes, wherein each node in a layer of the neural network corresponds to a portion of the material and assigned a value the permittivity of the portion of the material, such that the values of the nodes at locations of the portions form the image of the distribution of the permittivity of the material, and wherein connections between layers in the neural network models scattering events, and to update the values of the nodes reducing an error between the measured set of echoes and the simulated set of echoes to produce the image of the distribution of the permittivity of the material.

Yet another embodiment of the invention discloses a non-transitory computer readable storage medium embodied thereon a program executable by a processor for performing a method that includes requesting to propagate a pulse of wave through the material to receive a set of echoes resulted from scattering the pulse by different portions of the material; simulating a propagation of the pulse in the material using a neural network to determine a simulated set of echoes, wherein each node in a layer of the neural network corresponds to a portion of the material and assigned a value the permittivity of the portion of the material, such that the values of the nodes at locations of the portions form the image of the distribution of the permittivity of the material, and wherein connections between layers in the neural network models scattering events; and updating the values of the nodes reducing an error between the received set of echoes and the simulated set of echoes to produce the image of the distribution of the permittivity of the material.

DETAILED DESCRIPTION OF THE PREFERRED EMBODIMENT

Figure 1:
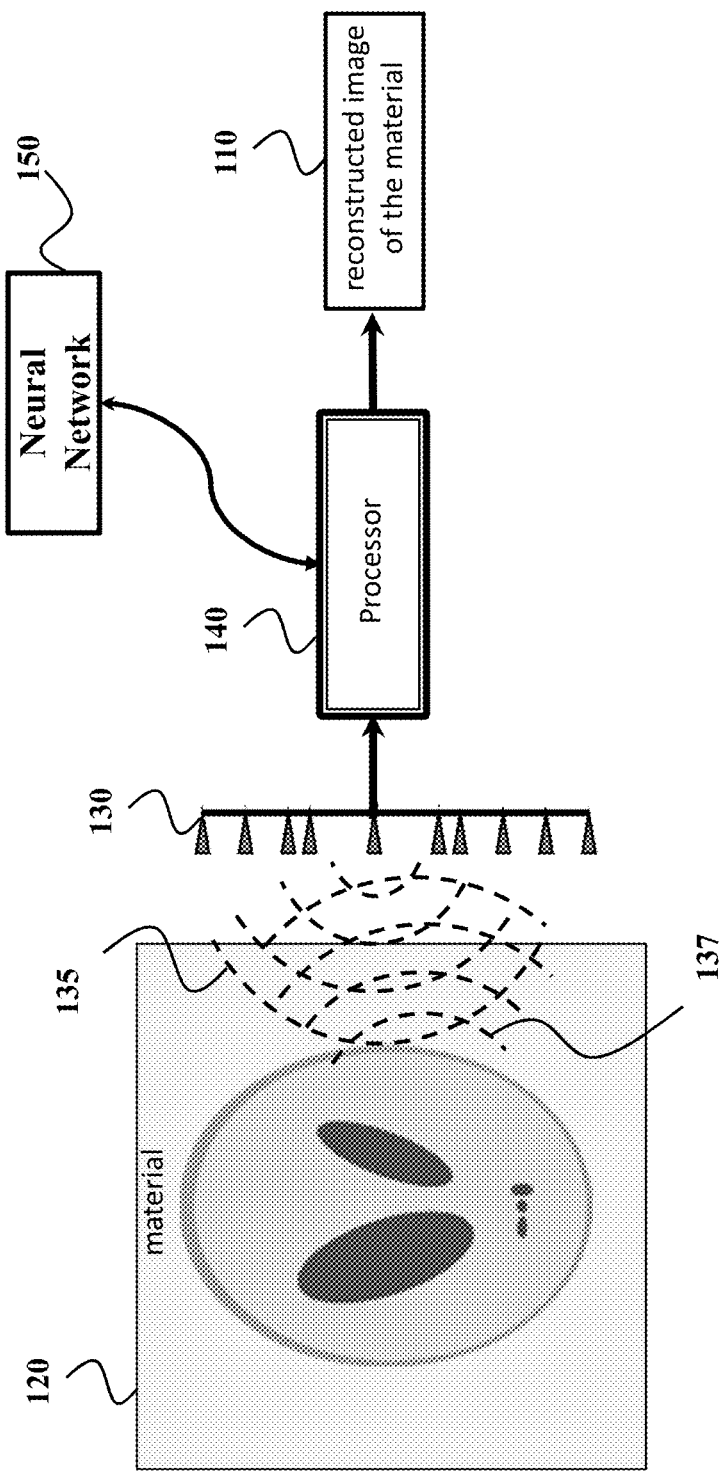
FIG. 1 is a block diagram of a permittivity sensor for determining an image of a distribution of permittivity of a material according to one embodiment of the invention.

FIG. 1 shows a block diagram of a permittivity sensor for determining an image 110 of a distribution of permittivity of a material 120 according to one embodiment of the invention. The permittivity sensor includes at least one transceiver 130 to propagate a pulse of wave 135 through the material 120 and to receive a set of echoes 137 resulted from scattering the pulse by different portions of the material.

For example, the transceiver can include at least one transmitter that transmits the pulse through the material, such that the pulse scattered by the material produces the set of echoes 137. The pulse can be any type of electromagnetic or optical waves, such as one or combination of a microwave pulse, a radar pulse, a laser pulse, an ultrasound pulse, an acoustic pulse. The transceiver can also include at least one receiver arranged at a predetermined location with respect to the transmitter for receiving the set of echoes 137. According to different embodiments, the permittivity sensor can produce a two- or three-dimensional image of the material, where each location in the image provides the value of the dielectric permittivity for a portion of material corresponding to that location.

The permittivity sensor also includes a processor 140 operatively connected with the transceiver 130 to determine the image 110 based on the set of echoes 137. In order to account for multiple scattering, the processor uses a neural network 150, where each node is the value of permittivity.

The processor simulates a propagation of the pulse in the material using the neural network 150 to determine a simulated set of echoes and updates the values of the nodes reducing an error between the received set of echoes and the simulated set of echoes to produce the image 110 of the distribution of the permittivity of the material.

Figure 2A:
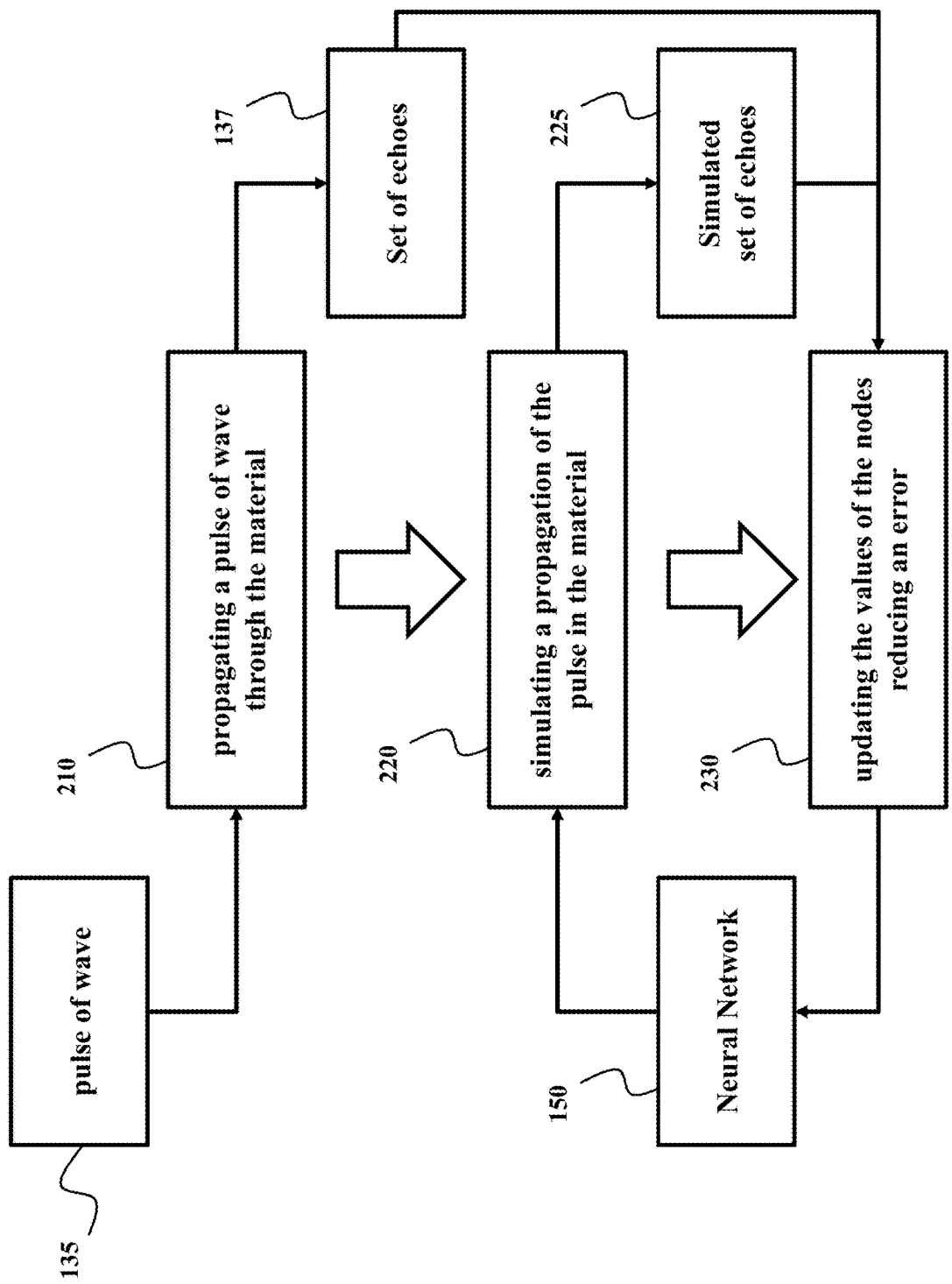
FIG. 2A is a block diagram of a method for determining the image of a distribution of the permittivity of the material according to some embodiments of the invention.

FIG. 2A show a block diagram of a method for determining an image of a distribution of permittivity of a material according to some embodiments of the invention. The method can be implemented using the processor 140. For example, the method can be implemented by the processor executing a program embodied on a non-transitory computer readable storage medium.

The method propagates 210 a pulse of wave 135 through the material to receive a set of echoes 137 resulted from scattering the pulse by different portions of the material. The method also simulates 220 a propagation of the pulse in the material using a neural network 150 to determine a simulated set of echoes 225. In some embodiments, each node in a layer of the neural network 150 corresponds to a portion of the material and assigned a value the permittivity of the portion of the material, such that the values of the nodes at locations of the portions form the image of the distribution of the permittivity of the material. Also, the propagation between two layers in the neural network models a scattering event, as described below. The method further updates 230 the values of the nodes in the network 150 by reducing an error between the received set of echoes and the simulated set of echoes to produce the image of the distribution of the permittivity of the material.

Figure 2B:
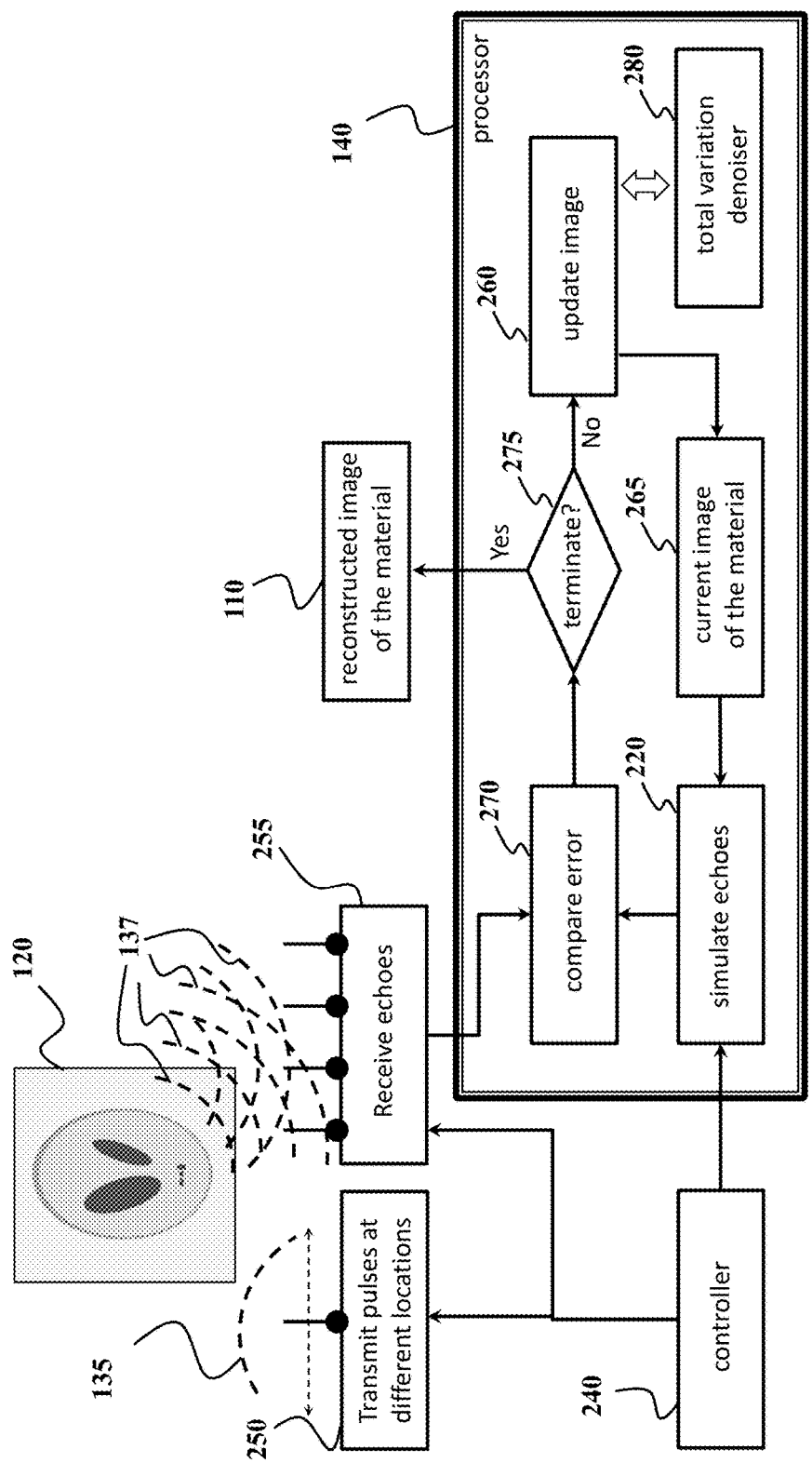
FIG. 2B is an exemplar implementation of the method of FIG. 2A.

FIG. 2B show a schematic of implementation of the method of FIG. 2A according to one embodiment of the invention. The method can be implemented using the processor 140. The processor, directly or through a controller 240, requests to propagate a pulse of wave through the material. For example, the processor, directly or through a controller 240, transmits 250 the pulse 135 through the material, such that the pulse scattered by the material produces the set of echoes 137. Also, the processor, directly or through a controller 240, receives 255 the set of echoes 137. The processor can also request to transform, the received set of echoes into a digital signal using an analog-to-digital converter and to record amplitude and/or other properties of the digital signal.

In some embodiments the processor updates the neural network 150 iteratively. For example, for each iteration, the processor simulates the set of echoes using the neural network and compares 270 the results of the simulation with the received set of echoes 255. The processor updates 260 the network 150 to produce a current image 265 of the distribution of permittivity. The iterations are repeated until a termination condition 275 is met. Examples of the termination condition include a maximal number of iterations and/or the size of the error. In some embodiments, additional transmitted and reflected pulses, as well as total variation denoising 280 are used to further improve the image to better fit the measurements.

Some embodiments of the invention are based on realization that scattering of a pulse of wave propagated through a material of an object can be represented by a neural network with varying functions of the nodes of the network and fixed numeric weights connecting the nodes. The functions of the nodes represent permittivity of different portions of the material and the weights of the connections represent the physics of scattering the pulse by corresponding portions of the material. Such a neural network can capture the nonlinearity of scattering the pulse by different portions of the material in a manner allowing determining the permittivity of the material of the object from effects of the permittivity on the result of the scattering.

The neural networks are a family of models inspired by biological neural networks and are used to estimate or approximate functions that can depend on a large number of inputs and are generally unknown. The neural networks are generally presented as systems of interconnected nodes or "neurons" that exchange messages between each other. Each node is associated with a function for transforming the message. This function is usually non-linear to form a non-linear part of message transformation. Each connection between the nodes is associated with a numeric weight for scaling of the messages to form a linear part of message transformation. Typically, the functions are fixed and predetermined for all nodes, e.g., selected by a designer of the neural network. Examples of the functions typically selected for the nodes include the sigmoid and rectifier function. In contrast, the numeric weights are different and tuned based on experience, making the neural network adaptive to inputs and capable of learning.

However, in the neural network used by different embodiments of the invention, such a relationship is reversed, i.e., the functions of the nodes are varied and determined during the training of the neural network, and the numeric weights of the connections between the nodes are fixed. Some embodiments of the invention are based on recognition that regardless of such a reverse relationships, the values of the nodes of the neural network can be learned using a back-propagation within amount of time comparable with the amount of time required for training the usual neural networks.

Figure 3:
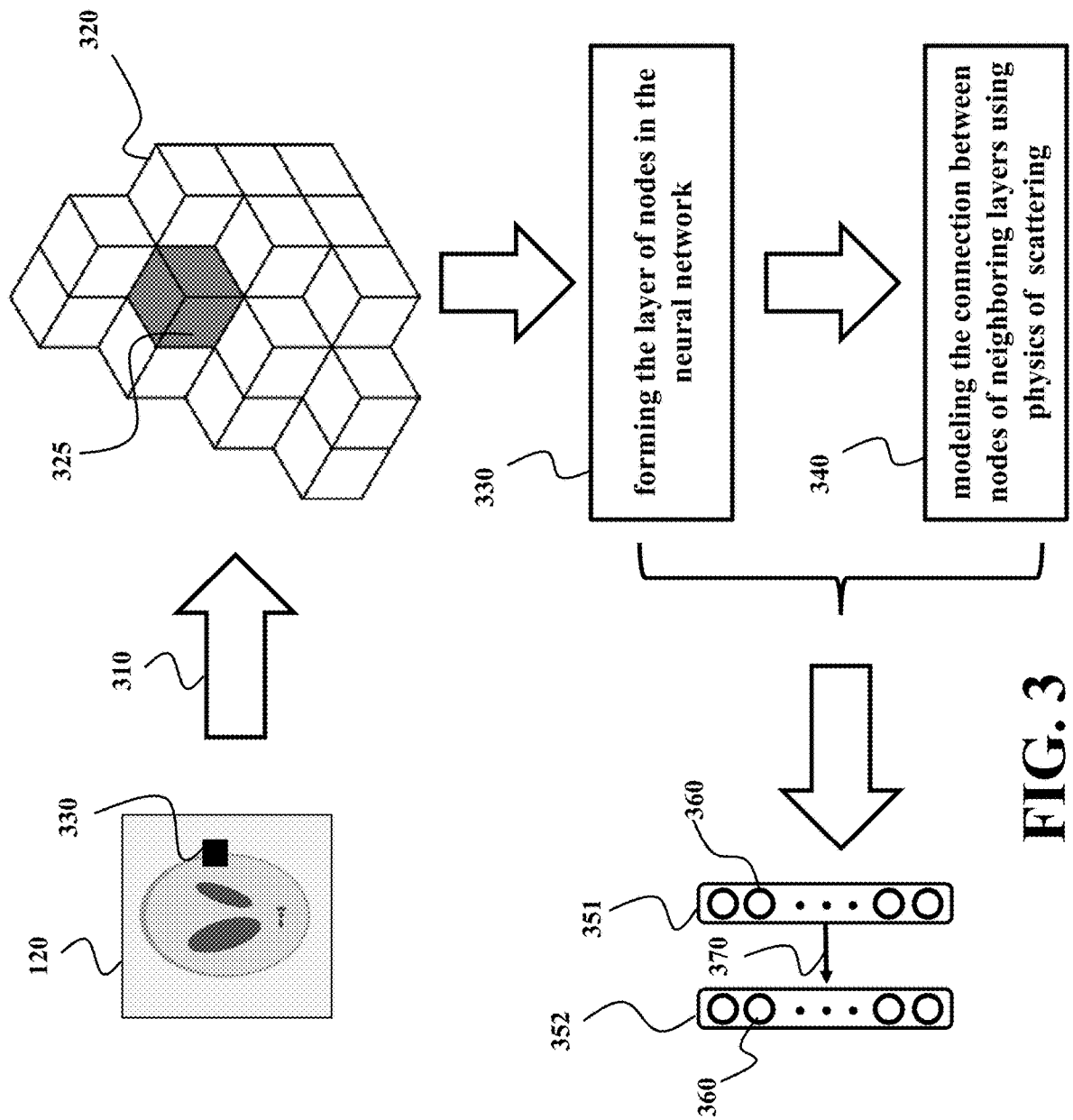
FIG. 3 is a schematic of formulation of a neural network according to one embodiment of the invention.

FIG. 3 shows a schematic of formulation of the neural network according to one embodiment of the invention. The material 120 is represented 310 as a combination 320 of a set of portions of the material. Each portion, e.g., a portion 325 has a corresponding location in the material, e.g., a location 330. By way of analogy, the portions 325 can be thought of as pixels of the image 110 if the image 110 is two-dimensional or voxels of the image 110 if the image 110 is three-dimensional. In the example of FIG. 3, the portions 320 are voxels of the three-dimensional image 110.

In some embodiments, the number of portions 320 corresponds to the resolution of the image 310. To that end, one embodiment determines a resolution of the image defining a number of pixels or voxels in the image and determines the set of portions according to the resolution of the image, such that each portion of the material corresponds to a pixel in the image. For example, for the desired resolution of 80×60 pixels in the image 110, the combination 320 has 4800 portions.

The embodiment forms 330 a layer 351 of the neural network using a set of nodes having one-to-one relationship with the set of portions of the material. Each node in the set corresponds to only one portion of the material. For example, the node 360 corresponds to the portion 325. The layers are repeated as many times as desired to represent an additional scattering event. To that end, the layers 351 and 352 are identical. For example, 30 layers of the network 150 represent 30 scattering events from each portion of the material.

The connection 370 between the nodes of the neural network 150 model 340 the scattering of the pulse by convolving the nodes in neighboring layers with a function of physics of the scattering. For example, one embodiment uses Green's function to model the physics of the scattering.

Simulation

Some embodiments of the invention address a scattering problem, where a material of dielectric permittivity distribution $\varepsilon(X)$, with $x=(x, y, z) \in \Omega$ and $\Omega \subseteq \mathbb{R}^3$, is immersed into the background medium of permittivity $\varepsilon_b$. The sources that generate the excitation pulses and sensors collecting the data are located in the sensor region $\Gamma \subseteq \mathbb{R}^3$. The incident electric field created by the lth source, located at $x_l \in \Gamma$, is denoted as $u_{in}(x, x_l)$ for all $x \in \mathbb{R}^3$.

The Lippmann-Schwinger equation describes the relationship between the permittivity and the wave-field in the material as $$u(x,x_l)=u_{in}(x,x_l)+\int_\Omega g(x-x')f(x')u(x', x_l)\,dx', \quad (1)$$

for all $x \in \Omega$, where we define the scattering potential $$f(x) \triangleq k_b^2(\varepsilon_b-\varepsilon(x)), \quad (2)$$

and the Green's function for the homogeneous medium $g(x)$. Similarly, the scattered field in the sensor region can be expressed as $$u_{sc}(x, x_\ell) = u(x, x_\ell) - u_{in}(x, x_\ell) \quad (3)$$

$$= \int_\Omega g(x - x')f(x')u(x', x_\ell)dx' \quad (4)$$

for any $x \in \Gamma$. Note that the integrals (1) and (4) extend only over $\Omega$ because the scattering potential $f$ is zero for all $x \notin \Omega$.

Various embodiments determine the function $f$, which is equivalent to dielectric permittivity $\varepsilon$, given transmissions by L sources, where each transmission includes M measurements of $\{u_{sc}^l(x_m,x_l)\}_{m\in[1\ldots M]}$ in $\Gamma$. Notably, the internal field $u=u_{in}+u_{sc}$ inside the integral depends on $u_{sc}$, which highlights the nonlinear nature of the problem.

The recursive algorithm for simulating the scattered wave at the sensor locations can be specified as follows $$Z_m \leftarrow \Sigma_{n=1}^N H_{mn} U_n^K f_n, \quad (5)$$

$$u_n^k \leftarrow u_n^0 + \Sigma_{i=1}^N G_{ni} u_i^{K-1} f_i \quad (6)$$

where m=1, ..., M, k=1, ..., K, n=1, ..., N. Here, the vector $f \in \mathbb{R}^N$ is the discretization of the scattering potential $f$, $z \in \mathbb{C}^M$ is the predicted scattered wave $u_{sc}$ at sensor locations $\{x_m\}_{m\in[1\ldots M]}$, $u^0 \in \mathbb{C}^N$ is the discretization of the input field $u_{in}$ inside $\Omega$, $H \in \mathbb{C}^{M\times N}$ is the discretization of the Green's function at sensor locations, $G \in \mathbb{C}^{N\times N}$ is the discretization of the Green's function inside $\Omega$. For every $k \in [1,\ldots K]$, the vector $u^k \in \mathbb{C}^N$ denotes discretized version of the internal field after k scatterings. One embodiment recursively updates the discretized version of the wave field to satisfy the field equation (3-4).

Figure 4A:
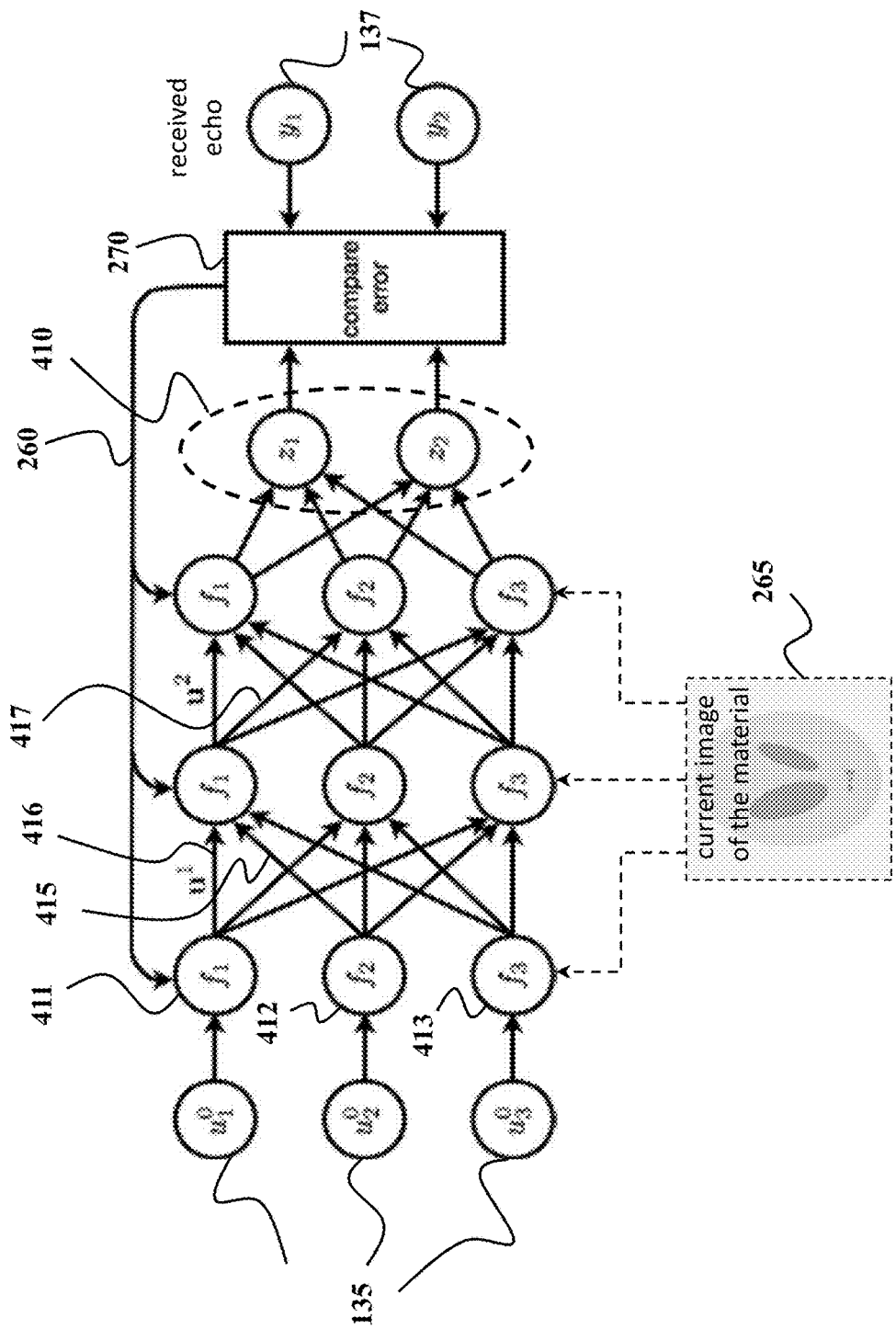
FIG. 4A is a schematic of a simulation of the propagation of the pulse through the material using the neural network according to one embodiment of the invention.

FIG. 4A shows a schematic of a simulation of the propagation of the pulse through the material using the neural network 150 according to one embodiment of the invention. The pulse 135, denoted by the vector $u^0$, is propagated through the network 150, where nodes 411, 412, and 413 correspond to different portions of f, which represents the current estimate of the permittivity image of the material. At the first layer, the pulse is first multiplied component-wise by the permittivity of the material f, and the result is convolved by the Green's function G represented as edges 415, 416 in the network 150 and $u^0$ is added after the convolution. The result of the convolution corresponds to the first scattering event and is represented as a vector $u^1$ in FIG. 4A. The same operation of component-wise multiplication by f, convolutions by G, and addition of $u^0$ is repeated at each of K layers as given by equation (6). In the final layer 410, the matrix H is applied to the product of the field $u^K$ and the current image of the material f to result in the simulated echo. The matrices H and G correspond to the convolution operators and can be implemented with a fast Fourier transform (FFT) algorithm. Therefore, the total computational cost of evaluating one forward pass through the network is of order z,58 (KN log (N)).

Figure 4B:
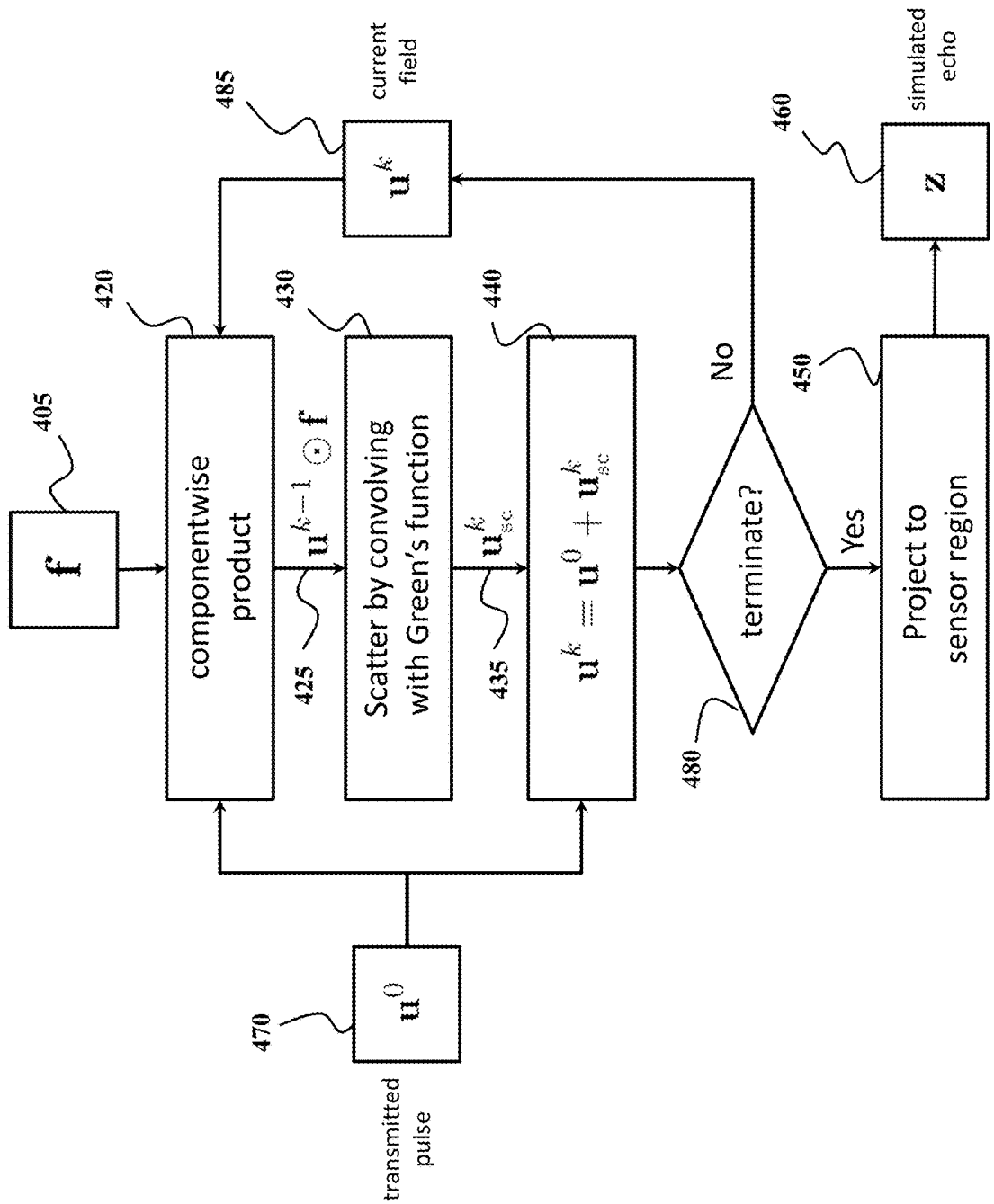
FIG. 4B is a block diagram of a method for simulation of the propagation of the pulse through the material according to one embodiment of the invention.

FIG. 4B shows a block diagram of a method for simulation of the propagation of the pulse through the material according to one embodiment of the invention. In this example, the current image 405 of the distribution of permittivity of the material is multiplied component-wise 420 with the transmitted pulse 470. The result of the product 425 is convolved with G 430 to yield the k-th scattered field 435. This scattered field is added 440 to the transmitted pulse 470 to provide the current field after k-th scattering event. This scattering process is repeated until a termination condition 480 is met. Examples of the termination condition include a maximal number of K scattering events. After termination, the field $u^K$ is projected 450 to the sensor region by multiplication with the matrix H to yield the simulated echo 460.

Updating Image

The image is updated by making a step towards minimization of an error function $$\mathcal{C}(f) = \mathcal{D}\text{D}(f) + \tau \mathcal{R}(f), \quad (7)$$

where $\mathcal{D}$ and $\mathcal{R}$ are is the data-fidelity and regularization terms, respectively, and $\tau > 0$ controls the amount of regularization. The physical constraints, such as for example non-negativity of the scattering potential, are enforced by projecting the image to a convex set $\mathcal{F} \subseteq \mathbb{R}^N$. The data-fidelity term is given by $$\mathcal{D}(f) \triangleq \frac{1}{2}\|y - z(f)\|_{\ell_2}^2,$$

where $y \in \mathbb{C}^M$ contains measurements of the scattered wave and z is the field simulated by our network. As a regularization term, we propose to use isotropic total variation penalty $$\mathcal{R}(f) \triangleq \sum_{n=1}^{N} \|[Dx]_n\|_{\ell_2} = \sum_{n=1}^{N} \sqrt{|[D_x f]_n|^2 + |[D_y f]_n|^2},$$

where D: $\mathbb{R}^N \to \mathbb{R}^{N \times 2}$ is the discrete gradient operator with matrices $D_x$ and $D_y$ denoting the finite difference operations along x and y directions, respectively.

A single step (7) of optimization is performed by using a proximal-gradient scheme or its accelerated variant as follows $$f \leftarrow \text{prox}_{\gamma \tau \mathcal{R}}(f^{-1} - \gamma \nabla \mathcal{D}(f^{-1})), \quad (8)$$

where $\gamma > 0$ is a step-size and $$\text{prox}_{\tau R}(g) \triangleq \underset{f \in \mathcal{F}}{\text{argmin}}\left\{\frac{1}{2}\|f - g\|_{\ell_2}^2 + \tau \mathcal{R}(f)\right\} \quad (9)$$

is the proximal operator, which corresponds to total variation denoising. Note that, although, the proximal operator for isotropic total-variation does not admit a closed form, it can be numerically computed. The gradient $\nabla \mathcal{D}$ can be obtained by evaluating $$\nabla \mathcal{D}(f) = Re\left\{\left[\frac{\partial}{\partial f} z(f)\right]^H (z(f) - y)\right\}, \quad (10)$$

where the Hermitian transposition H is due to the complex nature of quantities. We adopt the following convention for the Jacobian $$\frac{\partial}{\partial f} z(f) \triangleq \left[\frac{\partial z}{\partial f_1} \cdots \frac{\partial z}{\partial f_N}\right]. \quad (11)$$

Then, by differentiating equations in (0) with respect to f and simplifying the resulting expressions, we have for any vectors $b \in \mathbb{C}^M$ and $r \in \mathbb{C}^N$ $$\left[\frac{\partial z}{\partial f}\right]^H b = (H^H b) \odot \bar{u}^K + \left[\frac{\partial u^K}{\partial f}\right]^H ((H^H b) \odot f)$$

$$\left[\frac{\partial u^k}{\partial f}\right]^H r = (G^H r) \odot \bar{u}^{k-1} + \left[\frac{\partial u^{k-1}}{\partial f}\right]^H ((G^H r) \odot f),$$

where k=1, . . . K, vector $\bar{v}$ contains complex conjugated elements of v, and operator $\odot$ denotes a component-wise multiplication between two vectors. These relationships lead to the following error backpropagation algorithm $$g^k \leftarrow g^K + 1 + [G^H r^k + 1] \odot \bar{u}^k \quad (12)$$

$$r^{k} \leftarrow [G^H r^{k+1}] \odot f, \quad (13)$$

where k=K-1, K-2, . . . , 0, with the initialization $r^K = [H^H(z-y)] \odot f$ and $g^K = [H^H(z-y)] \odot \bar{u}^K$. The final expression for the gradient (10) is finally obtained by returning $\nabla_{\mathcal{D}}(f) = Re\{g^0\}$.

The error backpropagation allows to efficiently evaluate the gradient of the scattered wave with respect to the scattering potential. Due to the convolutional structure of the matrices, its computational complexity is equivalent to running a forward pass, which is of order $\mathcal{O}$ (KN log (N)). Equipped with this algorithm, the scattering potential can be optimized by using iteration (8). Note that the algorithm circumvents the need to explicitly evaluate and store the Jacobian (11) by directly computing its product with the residual b=(z-y).

Figure 5:
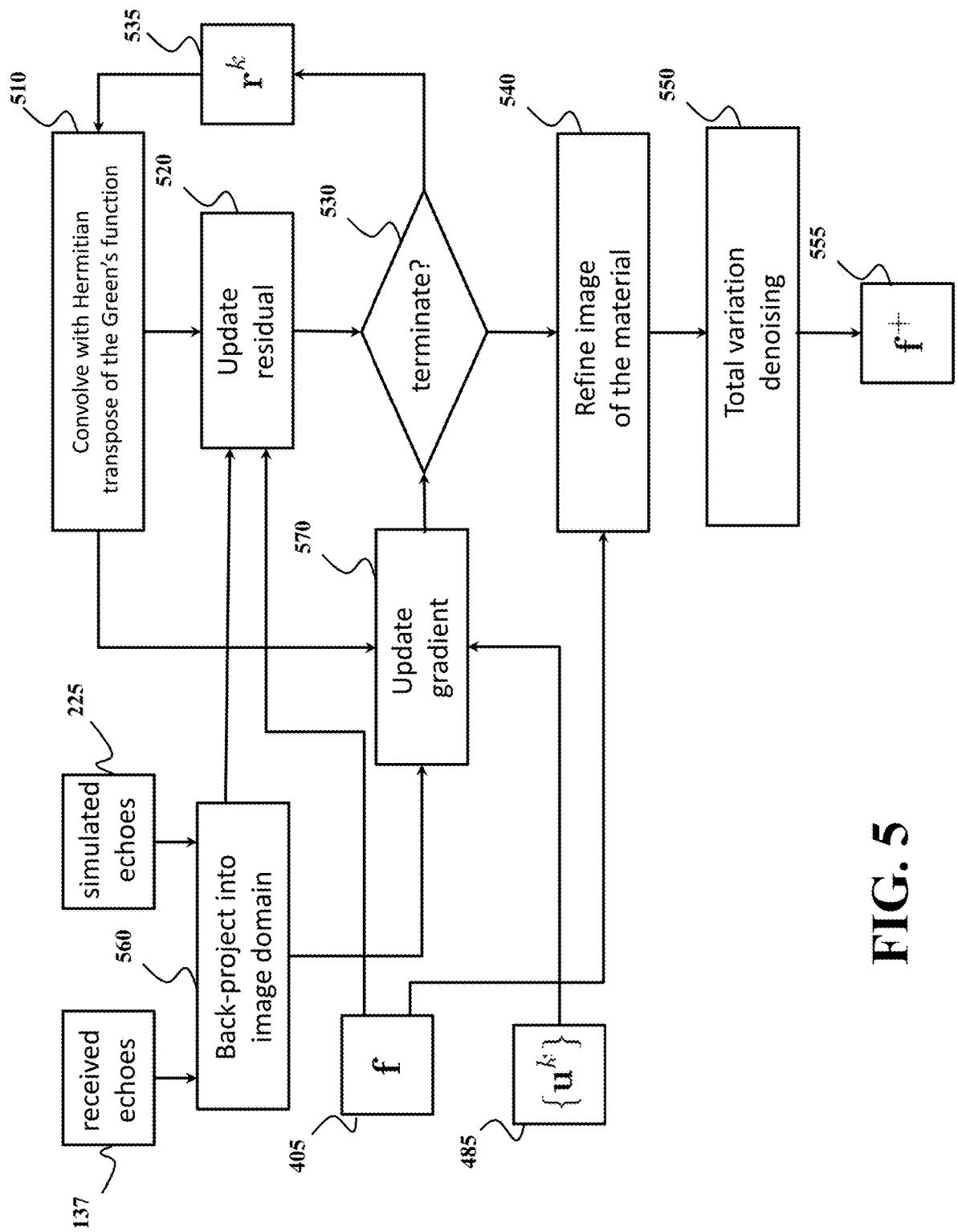
FIG. 5 is a block diagram of a method for updating the image of the distribution of permittivity of a material according to one embodiment of the invention.

FIG. 5 shows a block diagram of a method for updating a current image 405 of a distribution of permittivity of a material according to one embodiment of the invention. The received echoes y 137 are subtracted from simulated echoes z 225, and the result of the subtraction is back-projected 560 $H^H(z-y)$ to the image domain. Next the method produces or updates 520 the current residual $r^K$ 535 by combining the back-projected image with current image 405. The updated residual 535 convolved 510 with Hermitian transpose of the Green's function and total scatter field 485 is used to update 570 the gradient of permittivity with respect to the current image 405, e.g., using the equation (12). This process is repeated until a termination condition 530 is met. Examples of the termination condition include reaching the first layer of the network 150. Finally, the image of the material is refined 540 and denoised 550 with total variation, which gives the updated material 555.

Figure 6:
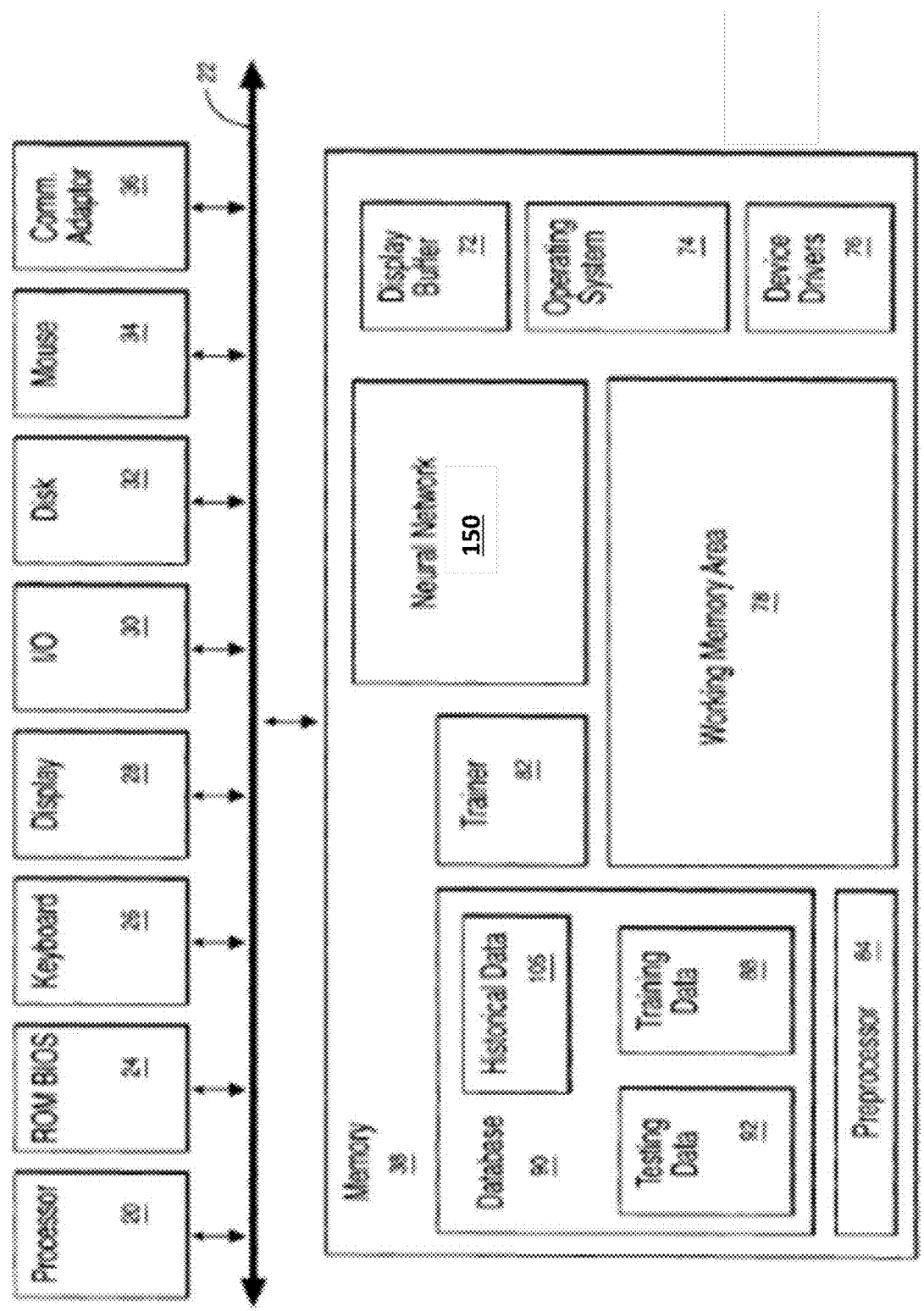
FIG. 6 is a block diagram of exemplar components of a permittivity sensor according to one embodiment of the invention.

FIG. 6 shows a block diagram of exemplar components of a permittivity sensor according to one embodiment of the invention. The permittivity sensor includes a processor 20 connected by a bus 22 to a read only memory (ROM) 24 and a memory 38. The permittivity sensor can also include a display 28 to present information, e.g., the image 110, to the user, and a plurality of input devices including a keyboard 26, mouse 34 and other devices that may be attached via input/output port 30. Other input devices such as other pointing devices or voice sensors or image sensors can also be attached. Other pointing devices include tablets, numeric keypads, touch screen, touch screen overlays, track balls, joy sticks, light pens, thumb wheels etc. The I/O 30 can be connected to communications lines, disk storage, input devices, output devices or other I/O equipment. The memory 38 includes a display buffer 72 that contains pixel intensity values for a display screen. The display 28 periodically reads the pixel values from the display buffer 72 displaying these values onto a display screen. The pixel intensity values may represent grey-levels or colors.

The memory 38 can include a database 90, a training module or trainer 82, the GLN 200, a preprocessor 84. The memory 38 can be any a non-transitory computer readable medium. The database 90 can include the historical data 105, training data, testing data 92. The database may also include results from operational, training or retaining modes of using the neural network. In one embodiment, the training module 82 performs the update of the network 150. The network 150 can be initialized using one or combination of the testing 92, the historical 106 and the training 88 data.

Also shown in memory 38 is the operating system 74. Examples of operating systems include AIX, OS/2, and DOS. Other elements shown in memory 38 include device drivers 76 which interpret the electrical signals generated by devices such as the keyboard and mouse. A working memory area 78 is also shown in memory 38. The working memory area 78 can be utilized by any of the elements shown in memory 38. The working memory area can be utilized by the neural network 150, the trainer 82, the operating system 74 and other functions. The working memory area 78 may be partitioned amongst the elements and within an element. The working memory area 78 may be utilized for communication, buffering, temporary storage, or storage of data while a program is running.

Figure 7:
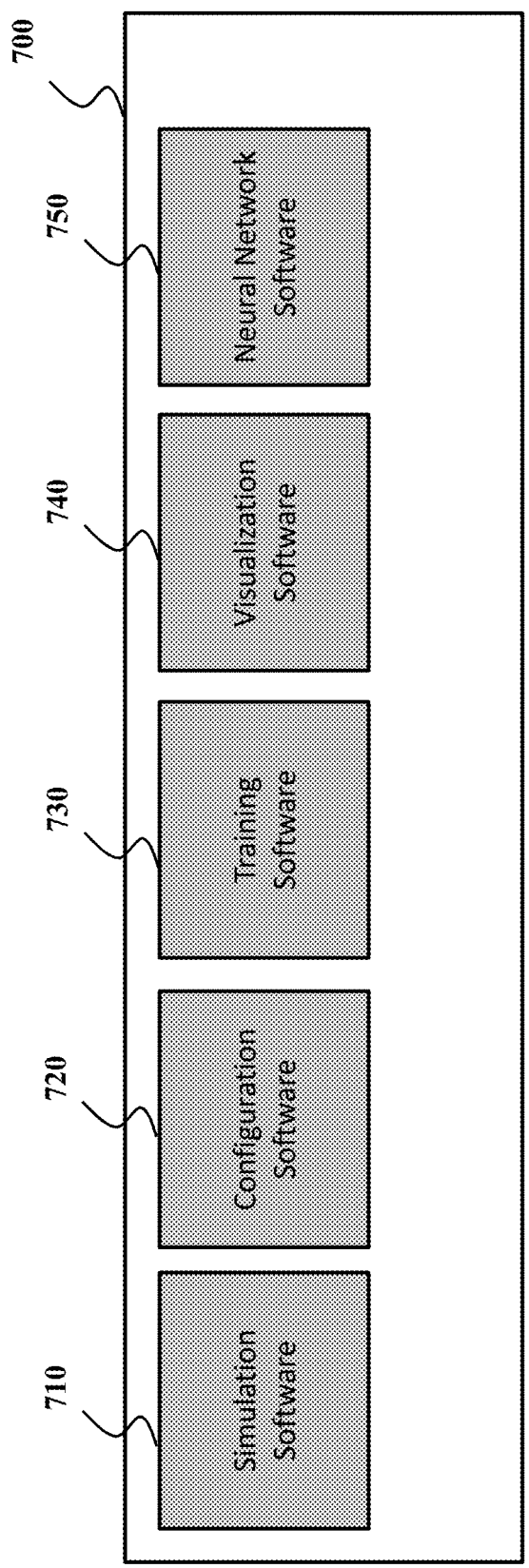
FIG. 7 is a schematic of an example of a non-transitory computer readable medium embodying thereon a program executable by a processor for performing methods according to different embodiments of the invention.

FIG. 7 shows an exemplar schematic of a non-transitory computer readable medium 700 embodied thereon a program executable by a processor for performing methods according to different embodiments of the invention. In this example, the program is organized in a number of software modules for executing different functions of the permittivity sensor.

For example, the simulation software 710 is responsible for simulating the propagation of the pulse through the material using the neural network 150. The configuration software 720 is responsible for selecting different parameters of the sensing, such as mutual arrangement between the receivers and transmitters of the permittivity sensor, dimension and resolution of the image 110, number of layers in the network 150. In some implementations, the configuration software directly or with help of the visualization software 740 receives the configuration parameters from the user of the permittivity sensor. Training software 730 performs the iterative updating of the image of the distribution of the permittivity of the material. Visualization software 740 serves to render the final image 110 on the display device to visualize the structure of the material to the user.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component. Though, a processor may be implemented using circuitry in any suitable format.

Also, the embodiments of the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Although the invention has been described by way of examples of preferred embodiments, it is to be understood that various other adaptations and modifications can be made within the spirit and scope of the invention. Therefore, it is the object of the appended claims to cover all such variations and modifications as come within the true spirit and scope of the invention.

We claim:

1. A method for determining an image of a distribution of permittivity of a material, comprising:

propagating a pulse of wave through the material, where the distribution of the permittivity of the material is initially unknown, to receive a set of echoes resulted from multiple scattering of the pulse of the wave propagating through the material by different portions of the material;

determining a synthesized set of echoes from the pulse of wave using a structure of a scattering neural network that is specific to an initial estimate of the distribution of the permittivity of the material, wherein each node in a layer of the structure of the scattering neural network corresponds to a portion of the material and assigned a value for an estimated permittivity of the portion of the material while the scattering neural network simulates a propagation of the pulse in the material, such that the values of the nodes at locations of the portions form the image of the distribution of the permittivity of the material, and wherein each layer in the scattering neural network corresponds to an additional scattering event, and wherein connections between layers in the scattering neural network models scattering events;

updating the values of the nodes based on determining iteratively the values of the nodes that reduce an error between the received set of echoes and the synthesized set of echoes to update the estimated permittivity of the material; and output the image of the distribution of the permittivity of the material based on the updated values of the nodes which was based on determining iteratively the values of the nodes that reduced the error between the received set of echoes and the synthesized set of echoes, wherein at least some steps of the method are performed by a processor.

2. The method of claim 1, wherein the propagating comprises:
transmitting, using a transmitter, the pulse through the material, such that the pulse scattered by the material produces the set of echoes;
receiving the set of echoes using at least one receiver arranged at a predetermined location with respect to the transmitter; and
transforming, the received set of echoes into a digital signal using an analog-to-digital converter; and
recording an amplitude of the digital signal.

3. The method of claim 1, wherein the simulating comprises:
representing the material as a combination of a set of portions of the material, each portion has a corresponding location in the material;
forming the layer of the scattering neural network using a set of nodes having one-to-one relationship with the set of portions of the material, such that each node in the set corresponds to only one portion of the material; and
modeling the scattering by convolving the nodes in neighboring layers with a function of physics of the scattering.

4. The method of claim 3, further comprising:
determining a resolution of the image defining a number of pixels or voxels in the image; and
determining the set of portions according to the resolution of the image, such that each portion of the material corresponds to a pixel or a voxel in the image.

5. The method of claim 3, further comprising:
adding a projection layer to the scattering neural network modeling projection of the set of echoes to the receiver through a medium bordering the material.

6. The method of claim 1, wherein the updating comprises:
determining iteratively the values of the nodes using a backpropagation with fixed numeric weights for connections between the nodes.

7. The method of claim 6, further comprising:
updating, for each iteration until a termination condition is met, the values of the nodes using a gradient descent minimization reducing the error between the received set of echoes and the synthesized set of echoes.

8. The method of claim 1, wherein the updating is performed iteratively until a termination condition is met, wherein an iteration comprises:
back-projecting a difference between the received set of echoes and the synthesized set of echoes into a domain of the image of the distribution of permittivity of the material to produce a back-projected image;
updating a residual by combining the back-projected image with a current image of the distribution of permittivity of the material;
convolving the updated residual with a Hermitian transpose of a Green's function; and updating the gradient of permittivity with respect to the current image using the convolved residual.

9. The method in claim 1, wherein the distribution of the permittivity is piecewise smooth, further comprising:
applying a total variation denoiser to enhance the image of the distribution of permittivity.

10. The method of claim 1, wherein the scattering neural network is a feedforward neural network.

11. The method of claim 1, further comprising:
rendering the image of the distribution of the permittivity of the material on a display device.

12. The method in claim 1, wherein each time the estimate of the distribution of the permittivity of material is updated, the scattering neural network is updated to be specific to a latest in time, estimate of the material.

13. The method in claim 1, wherein the scattering neural network captures a nonlinearity of scattering the pulse by different portions of the material, so as to determine the permittivity of the material of the object from effects of the permittivity as a result of the scattering.

14. The method in claim 1, wherein the structure includes varying functions of nodes representing permittivity of different portions of the material, along with fixed numeric weights connecting the nodes, where the weights of the connections represent a physics of scattering of the pulse by corresponding portions of the material.

15. A permittivity sensor for determining an image of a distribution of permittivity of a material, comprising:
at least one transceiver to propagate a pulse of wave through the material and to receive a set of echoes resulted from multiple scattering of the pulse of the wave propagating through the material by different portions of the material;
a processor is configured to:
determine a synthesized set of echoes from the pulse of wave using a structure of a scattering neural network that is specific to an initial estimate of the distribution of the permittivity of an initial estimate of the material, wherein each node in a layer of the structure of the scattering neural network corresponds to a portion of the material and assigned a value for an estimated permittivity of the portion of the material while the scattering neural network simulates a propagation of the pulse in the material, such that the values of the nodes at locations of the portions form the image of the distribution of the permittivity of the material, wherein each layer in the scattering neural network corresponds to an additional scattering event, and wherein connections between layers in the scattering neural network models scattering events, and to
update the values of the nodes based on determining iteratively the values of the nodes that reduce an error between the measured set of echoes and the synthesized set of echoes to update the estimated permittivity of the material, and
output the image of the distribution of the permittivity of the material based on the updated values of the nodes which was based on determining iteratively the values of the nodes that reduced the error between the received set of echoes and the synthesized set of echoes.

16. The permittivity sensor of claim 15, further comprising:
a display device, wherein the processor renders the image of the distribution of the permittivity of the material on the display device.

17. The permittivity sensor of claim 15, wherein the processor
represents the material as a combination of a set of portions of the material, each portion has a corresponding location in the material;
forms the layer of the scattering neural network using a set of nodes having one-to-one relationship with the set of portions of the material, such each node in the set corresponds to only one portion of the material; and models the scattering by convolving with Green's function.

18. The permittivity sensor of claim 15, wherein the processor determines iteratively the values of the nodes using a backpropagation with fixed numeric weights for connections between the nodes.

19. The permittivity sensor of claim 15, wherein the processor adds a projection layer to the scattering neural network modeling projection of the set of echoes to the receiver through a medium bordering the material and applies a total variation denoiser to enhance the image of the distribution of permittivity.

20. A non-transitory computer readable storage medium embodied thereon a program executable by a processor for performing a method, the method comprising:

requesting to propagate a pulse of wave through the material to receive a set of echoes resulted from multiple scattering of the pulse of the wave propagating through the material by different portions of the material;

determining a synthesized set of echoes from the pulse of wave using a structure of a scattering neural network that is specific to the distribution of the permittivity of the material, wherein each node in a layer of the structure of the scattering neural network corresponds to a portion of the material and assigned a value for an estimated permittivity of the portion of the material while the scattering neural network simulates a propagation of the pulse in the material, such that the values of the nodes at locations of the portions form the image of the distribution of the permittivity of the material, and wherein each layer in the scattering neural network corresponds to an additional scattering event, and wherein connections between layers in the scattering neural network models scattering events; and updating the values of the nodes based on determining iteratively the values of the nodes that reduce an error between the received set of echoes and the synthesized set of echoes to update the estimated permittivity of the material; and outputting the image of the distribution of the permittivity of the material based on the updated values of the nodes which was based on determining iteratively the values of the nodes that reduced the error between the received set of echoes and the synthesized set of echoes.

21. The medium of claim 20, wherein the method further comprises:

representing the material as a combination of a set of portions of the material, each portion has a corresponding location in the material;

forming the layer of the scattering neural network using a set of nodes having one-to-one relationship with the set of portions of the material, such each node in the set corresponds to only one portion of the material;

modeling the scattering by convolving with Green function; and adding a projection layer to the scattering neural network modeling projection of the set of echoes to the receiver through a medium bordering the material.

22. The medium of claim 20, wherein the method further comprises:

determining iteratively the values of the nodes using a backpropagation with fixed numeric weights for connections between the nodes.

* * * * *